United States Patent [19]
Cooke et al.

[11] Patent Number: 5,643,328
[45] Date of Patent: Jul. 1, 1997

[54] IMPLANTABLE CARDIAC STIMULATION DEVICE WITH WARNING SYSTEM HAVING ELONGATED STIMULATION ELECTRODE

[75] Inventors: Daniel J. Cooke; David Prutchi; Patrick J. Paul, all of Lake Jackson, Tex.

[73] Assignee: Sulzer Intermedics Inc., Angleton, Tex.

[21] Appl. No.: 684,429

[22] Filed: Jul. 19, 1996

[51] Int. Cl.⁶ .............................. A61N 1/362; A61N 1/05
[52] U.S. Cl. .............................. 607/36; 607/116
[58] Field of Search .............................. 128/642; 607/27, 607/29, 36–38, 115–116, 119

[56] References Cited

U.S. PATENT DOCUMENTS

| | | | |
|---|---|---|---|
| 4,140,131 | 2/1979 | Dutcher et al. | 128/419 PT |
| 5,076,272 | 12/1991 | Ferek-Petric | 607/29 |
| 5,388,578 | 2/1995 | Yomtov et al. | 607/37 |
| 5,549,653 | 8/1996 | Stotts et al. | 607/9 |

FOREIGN PATENT DOCUMENTS 42 13 993  12/1992  Germany .

*Primary Examiner*—William E. Kamm
*Assistant Examiner*—George R. Evanisko
*Attorney, Agent, or Firm*—John R. Merkling

[57] ABSTRACT

An implantable cardiac stimulation system having a patient warning system and an elongated electrode mounted near the can of the system for providing reliable stimulation for warning. The electrode has an extended length and a short width. The length is preferably at least double the width and more preferably at least four times the width. This extended length increases the probability that contact with the surrounding tissue will be achieved. The short width and rounded profile of the width, forming an "edge", on the other hand, increases the probability that a high enough current density will be achieved, causing stimulation to occur. The electrode may also be curved along its length, which tends to promote a "point" or small area contact between the electrode and the patient's tissue. The electrode may be mounted directly on the can or header of the cardiac stimulator or may be part of a separate pin electrode. If a pin electrode is used, a hood configuration can be used to surround at least part of the header, reducing rotation of the pin electrode. By making only a portion of the surface of the pin electrode conductive, and particularly edges or corners, an elongated electrode, as described herein, is formed which produces a higher electric current density and more efficient stimulation.

27 Claims, 4 Drawing Sheets

IMPLANTABLE CARDIAC STIMULATION DEVICE WITH WARNING SYSTEM HAVING ELONGATED STIMULATION ELECTRODE

FIELD OF OUR INVENTION

Our invention relates to cardiac pacemakers and other cardiac stimulators which monitor the operation of the heart and stimulate the heart tissue as required to maintain the proper operation of the heart, including implantable cardioverters and defibrillators. In particular, our invention relates to an implantable cardiac stimulating system with the capability of alerting or warning a patient of certain conditions or situations, including, without limitation, battery depletion, lead malfunction, or the eminent delivery of therapy.

BACKGROUND OF OUR INVENTION

It has long been known that the heart muscle provides its pumping function in response to electrical events which occur within the atrium and ventricle of the heart. Conductive tissue connects the atrium and the ventricle and provides a path for electrical signals between the two areas. In a normal heart, a natural atrial event spontaneously occurs in the atrium and a corresponding ventricular event occurs later in the ventricle. Synchronized electrical events occurring naturally in the atrium and ventricle cause the heart muscle to rhythmically expand and contract and thereby pump blood throughout the body.

In a diseased heart, atrial and ventricular events may not naturally occur in the required synchronized manner and the pumping action of the heart is therefore irregular and ineffective to provide the required circulation of blood. The required synchronized activity of such diseased hearts can be maintained by any implanted cardiac pacemaker which applies synchronized stimulating pulses to either the atrium or ventricle or both.

A diseased heart may also beat unusually quickly, a condition known as tachycardia, or may lapse into a rapid, disorganized quivering known as fibrillation. The former condition is undesirable; the latter condition may be fatal. To correct these conditions, implantable cardioverters and defibrillators have been proposed. Like the related cardiac pacemaker, these devices monitor the electrical condition of the heart and provide a corrective electrical therapy to correct the improper heart function. The three functions of pacing, cardioverting and defibrillating, or any of them, may be incorporated into a single device, generically, an implantable cardiac stimulator.

Cardiac stimulators am battery powered and, consequently, have a finite life before battery depletion may be expected. In addition to the battery, other components of the cardiac stimulation system may fail, such as leads, electrodes, or other system components. As an example of another type of change, the sensitivity of a patient's heart to electrical stimulation may change over time, altering the so-called threshold level for electrical stimulation. Such change of condition requires adaptation of the therapy delivered by the implantable cardiac stimulator, either automatically or by intervention by the attending physician. In any of these situations, or others, it may be deemed desirable to alert the patient to a changed condition so that action may be taken. For example, a pacemaker may detect the approaching end of life of its battery, in a known manner. It is desirable to alert the patient to this condition. Moreover, in the case of implantable defibrillators, delivery of therapy can be traumatic. It is sometimes deemed important to alert the patient to the prospect of eminent delivery of therapy.

Cardiac stimulators which alert or warn the patient of such conditions are known in the art. For example, such a device is described by Dutcher, et al. in U.S. Pat. No. 4,140,131. In the device described by Dutcher, et al., a device-controlled switch is activated to enable a specialized electrode adjacent the pacemaker to stimulate the patient's muscles to twitch. The nature of the electrode is not described in detail, but Ferek-Petric, in U.S. Pat. No. 5,076,272, described the electrode of Dutcher, et al., as an auxiliary electrode surrounded by the indifferent electrode and fixed on the pacemaker can. In contrast, Ferek-Petric describes a cardiac stimulator with patient warning with an electrode affixed to the header of the stimulator. Another electrode is described in U.S. patent application Ser. No. 08/426,949, filed Apr. 21, 1995, by some of us (Paul and Prutchi), also assigned to Intermedics, Inc.

SUMMARY OF OUR INVENTION

We have found that an elongated electrode mounted near the pacemaker can is effective in providing reliable stimulation for warning. The electrode has an extended length and a short width. The length is preferably at least double the width and more preferably at least four times the width. This extended length increases the probability that contact with the surrounding tissue will be achieved. The short width, on the other hand, increases the probability that a high enough current density will be achieved, causing stimulation to occur. Moreover, an edge profile further concentrates the current. An "edge" may be produced by, for example, either a raised area or bump or by a conjunction of two surfaces, as at a corner. The electrode may be mounted directly on the can or header of the cardiac stimulator or may be part of a separate pin electrode, as described in our U.S. patent application Ser. No. 08/532,961, now U.S. Pat. No. 5,549,653, and in a continuation-in-part application filed on the same date as this application. As described in the last two mentioned applications, a pin electrode can be mounted in one of two or more standard connector sockets in the header of a dual chamber pacemaker or multi-function cardiac stimulator to provide the necessary stimulus to the skeletal muscles of the patient to produce an effective twitch. A hood configuration can be used to surround at least part of the header, reducing rotation of the pin electrode. By making only a portion of the surface of the pin electrode conductive, and particularly edges or corners, an elongated electrode, as described herein, is formed which produces a higher electric current density and more efficient stimulation.

It is an object of our invention, therefore, to provide an elongated electrode for use in a patient warning system in an implantable medical device. It is also an object to provide means whereby a cardiac stimulator, capable of being programmed, may be modified to include a patient warning apparatus. It is a further object of our invention to provide an auxiliary electrode for the purpose of providing patient warning signals by stimulating excitable tissue of the patient, for example, nerve ends or voluntary muscles. It is a further object of our invention to provide for an effective implantable cardiac stimulation system with a reliable patient warning apparatus. With the foregoing in mind, we will now describe the preferred embodiment of our invention with respect to the accompanying drawings.

DETAILED DESCRIPTION OF OUR PREFERRED EMBODIMENT

Figure 1:
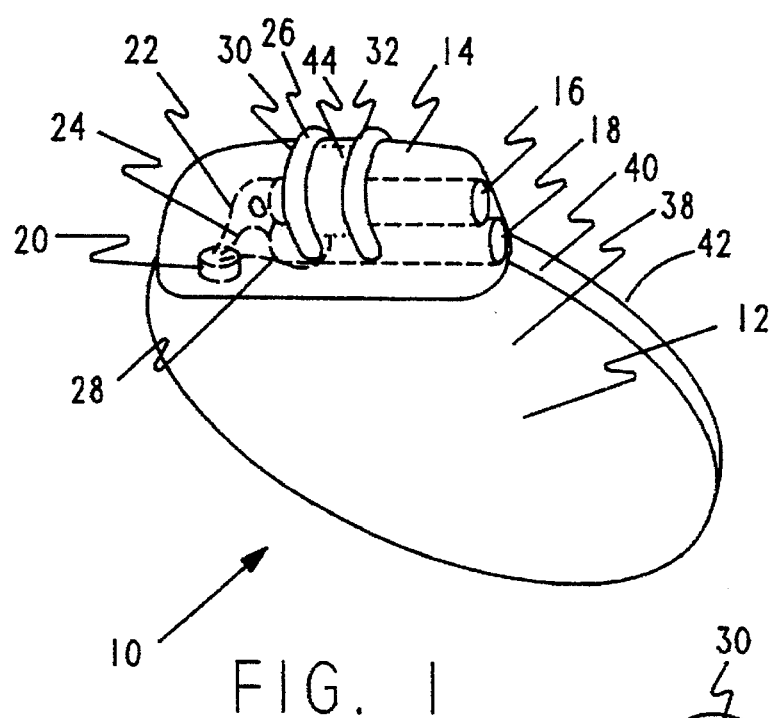
FIG. 1 is a perspective drawing of a dual chamber cardiac stimulator and warning electrode according to our invention.

FIG. 1 is a perspective drawing illustrating a cardiac stimulator, generally designated 10, according to our invention. We have illustrated our invention in connection with a dual chamber pacemaker, but our invention is equally applicable with other implantable cardiac stimulators such as cardioverters and defibrillators, as are known in the art. The cardiac stimulator 10 comprises a hermetically sealed case or can 12 which, in a known fashion, contains batteries and electrical circuitry. A header 14, attached to the can 12, has two sockets 16, 18 to which leads can be mechanically and electrically connected. Leads are commonly used to place the cardiac stimulator 10 in electrical communication with the heart or other body tissues. Electrical conductors 22, 24 provide an electrical connection between the sockets 16, 18 and the circuitry inside the can 12 through a feedthrough 20.

Figure 2:
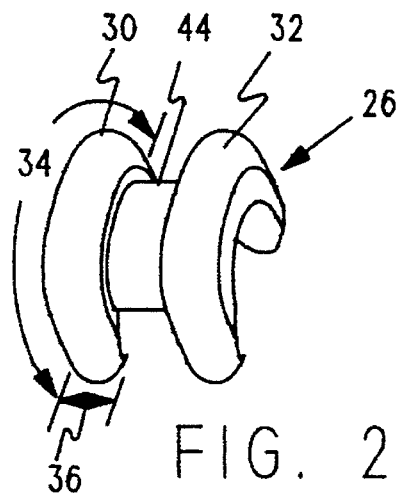
FIG. 2 is a perspective drawing of a warning electrode according to our invention.

A warning electrode 26 is mounted on the cardiac stimulator 10, preferably on the header 14. An electrical conductor 28 connects the warning electrode 26 to the circuitry inside the can 12 through the feedthrough 20. A preferred embodiment of the warning electrode 26 is more particularly illustrated in FIG. 2. As shown in FIG. 2, the warning electrode comprises at least one stimulating surface 30, and may comprise a plurality of such surfaces, such as the illustrated surfaces 30, 32. Each stimulating surface 30 has a length 34 and a width 36 orthogonal to said length 34. The length may be curved as shown, which we believe is advantageous because it tends to produce a point or small area of contact between the surface 30 and the surrounding tissue. The length may also, however, be made linear. Similarly, the width may be linear or curved. It is important, however, that the length be greater than the width, preferably at least twice the width, and more preferably at least four times the width. The length makes it likely that the stimulating surface will contact adjacent tissue when the cardiac stimulator 10 is implanted in the body of a patient. The relatively narrow width and relatively sharp profile, however, makes it likely that only a limited portion of the stimulating surface will contact adjacent tissue, thereby minimizing the actual conducting surface area and increasing the current density. The rounded or relatively sharp profile of the width forms an "edge", which also appears to concentrate the current density. Increased current density makes it more likely that effective stimulation will occur and that the patient will perceive the warning signal.

The stimulating surface 30 may also curve around the cardiac stimulator 10 from a front side 38 across an edge 40 to a back side 42 of the stimulator 10. Where more than one stimulating surface 30, 32 are provided, the length of each stimulating surface 30, 32 is preferably parallel to the lengths of the other stimulating surfaces. In our preferred embodiment, the two stimulating surfaces 30, 32 are connected by a saddle 44. With the two stimulating surfaces connected mechanically and electrically, it is easier to mount the warning electrode 26 on the cardiac stimulator, more specifically in the header. The warning electrode 26 may be pre-cast into the header, or the header may be formed by casting epoxy or another suitable material around the warning electrode and the sockets 16, 18. The header is usually non-conductive and preferably covers the saddle 44, leaving only the stimulating surfaces 30, 32 exposed.

In the can 12 of the cardiac stimulator 10, a microprocessor 46 preferably provides control and computational facilities. It will be appreciated that other forms of circuitry, such as analog or discrete digital circuitry, can be used in place of the microprocessor 46. However, a microprocessor is preferred for its miniature size and flexibility, both of which are of critical importance for the implantable systems in which it is envisioned our invention will find use. A particularly energy efficient microprocessor which is designed specifically for use in pacemakers is fully described in Gordon, et al, U.S. Pat. No. 4,404,972, which is assigned to the assignee of our invention. The disclosure thereof is incorporated herein by reference.

The microprocessor 46 has input/output ports connected in a conventional manner via a bi-directional bus 48 to memory 50, and interval timers 52, 54. Memory 50 preferably includes both ROM and RAM. The microprocessor 46 may also contain additional ROM and RAM as described in Gordon, et al., above. Generally, the pacemaker operating routine is stored in ROM or EPROM memory. RAM stores various programmable parameters and variables used in conjunction with the pacemaker operation. The interval timers 52, 54 may be external to the microprocessor 46, as illustrated, or internal thereto, as described in Gordon, et al., above. The timers 52, 54 are conventional up or down counters of a type initially loaded with count value and count up to or down from the value and output a roll-over bit on completing the programmed count. If the stimulator is used as a dual chamber pacemaker, the interval timers would be used to time AV and VA intervals. If the stimulator is used as a single chamber pacemaker, a timer would be used to time an A/A or V/V interval, depending on the chamber of the heart being sensed and paced.

The microprocessor 46 preferably has an input/output port connected to a telemetry interface 56. The implanted cardiac stimulator 10 is thus able to receive pacing, rate control, or other parameters from an external programmer through an antenna 58 and to send data to an external receiver if desired. Many suitable telemetry systems are known to those skilled in the art. One such system and coding arrangement is described in Calfee, et al. U.S. Pat. No. 4,539,992 which is also assigned to the assignee of our invention. That description is incorporated therein by reference.

Microprocessor output ports are connected to the input of a stimulus pulse generator 60, used to stimulate the atrium, by a control line 62. Similarly, a stimulus generator 64, ordinarily used to stimulate the ventricle, is connected to the microprocessor by a control line 66. The microprocessor 46 transmits pulse parameter data, such as pulse amplitude and width, as well as enable/disable and pulse initiation codes to the stimulus generators 60, 64 along their control lines 62, 66 respectively. The stimulus generators 60, 64 are connected to the heart 68 by leads 70, 72 with electrodes 74, 76 and will, under the control of the microprocessor, stimulate the atrium or the ventricle as determined by the pacemaker programming. Another stimulus generator 78, on the other hand, is controlled by control line and is connected to excitable tissue 82 by the conductor 28 and the warning electrode 26. The excitable tissue could be skeletal muscle, a nerve ending, or other tissue capable of a perceptible physiologic reaction in response to electrical stimulation. The electrical condition of the heart must also be sensed and that condition must be transmitted to the microprocessor 46. For this purpose, ventricular and atrial sense amplifiers 84, 86 are connected between the leads 72, 70 and the microprocessor 28. The ventricular sense amplifier 84 detects occurrences of R waves. An atrial sense amplifier 86 detects the occurrence of P waves.

Figure 4:
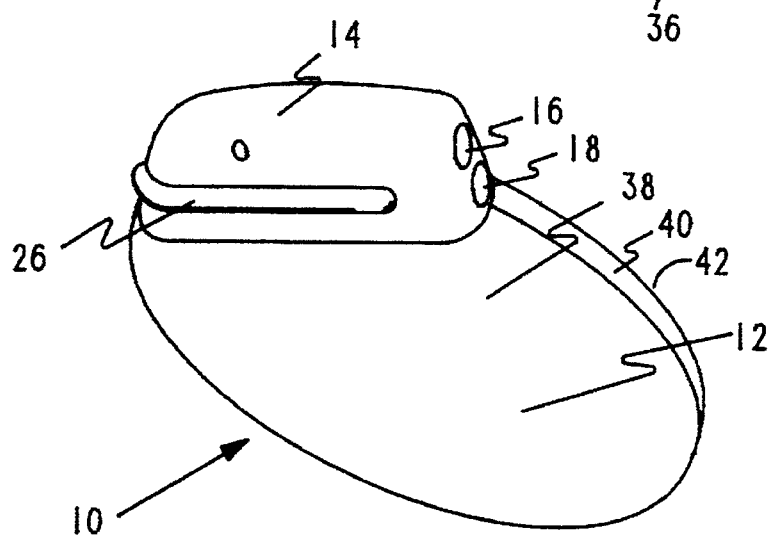
FIG. 4 is a perspective drawing of an alternative embodiment of the cardiac stimulator of FIG. 1.
Figure 3:
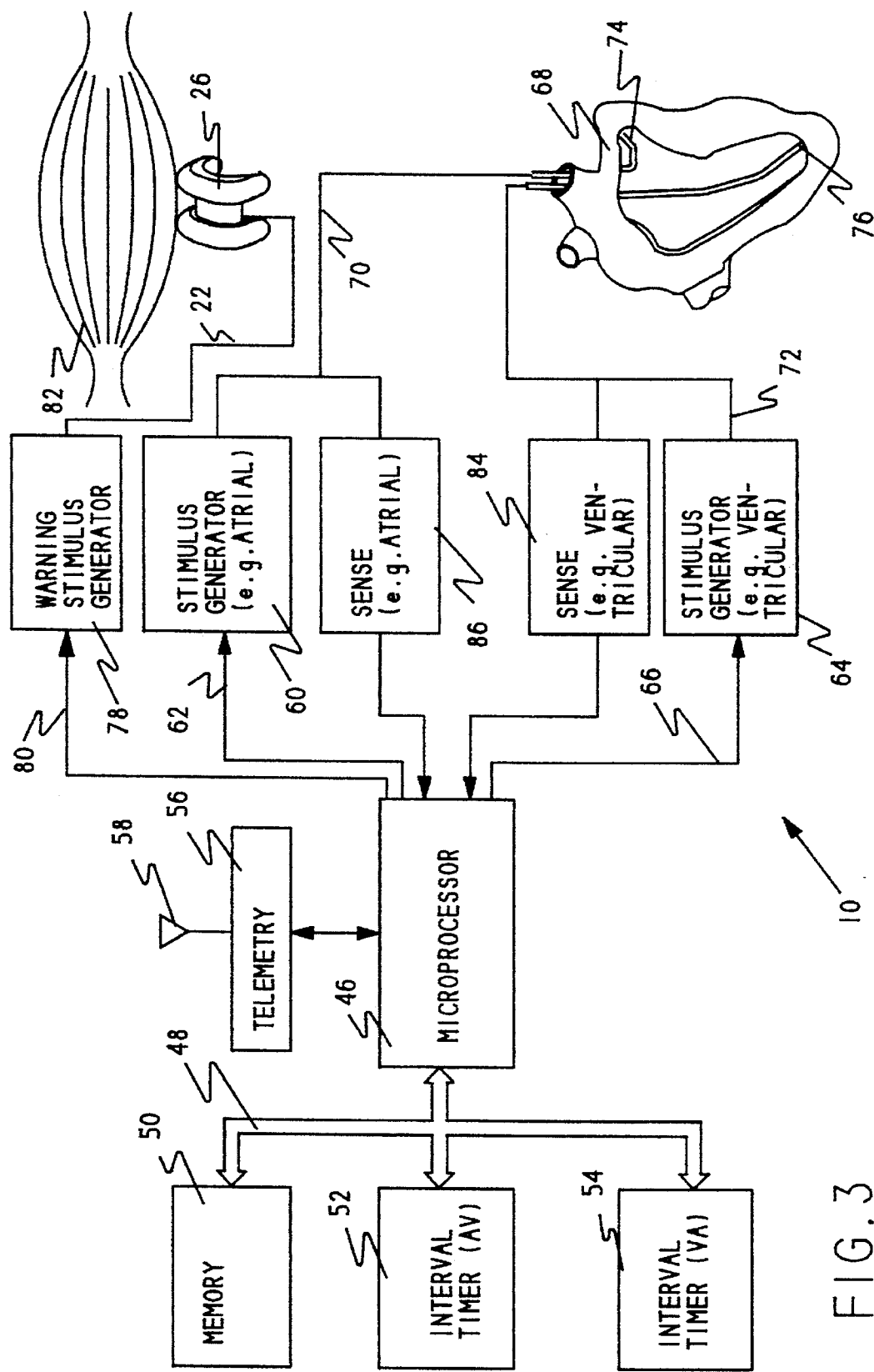
FIG. 3 is a block diagram of the cardiac stimulator of FIG. 1.

An alternative embodiment of our invention is shown in FIG. 4. In this embodiment, the warning electrode 26 does not pass over the header 14 as shown in FIG. 1, but rather extends along the header, substantially parallel to the sockets 16, 18. As above, the electrode can extend from the front side 38 of the cardiac stimulator 10, across the edge 40 and to the back side 42.

Figure 6:
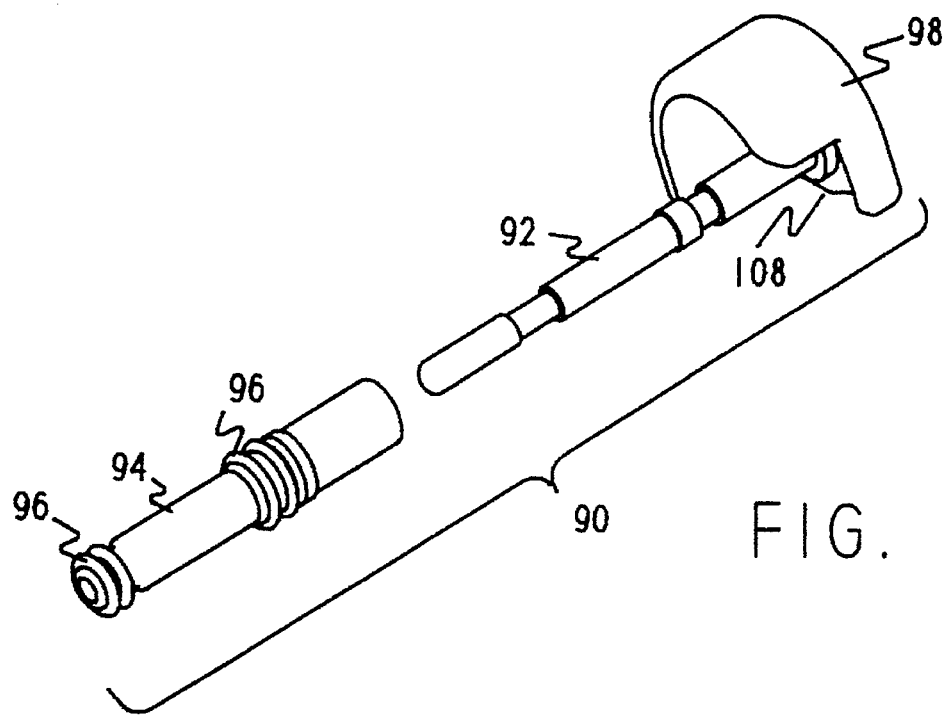
FIG. 6 is an exploded perspective view of a pin-type warning electrode.
Figure 5:
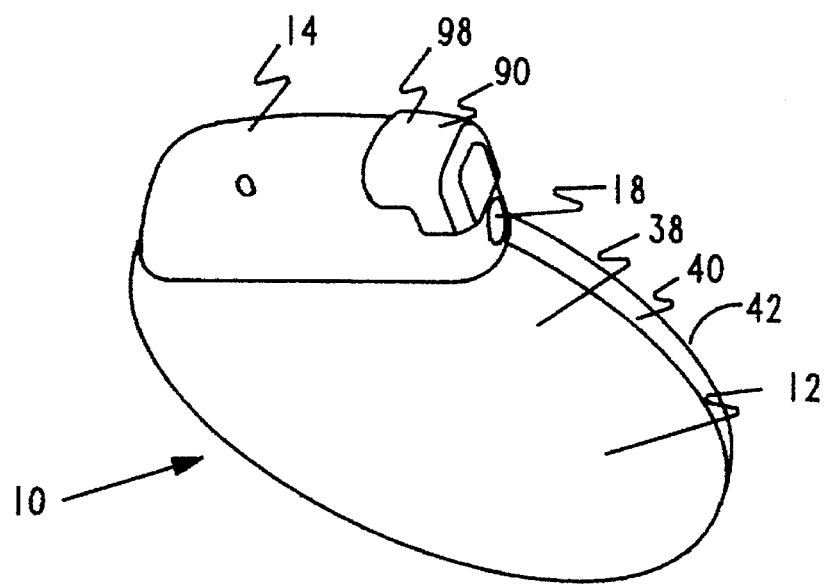
FIG. 5 is a perspective drawing of an alternative embodiment of the cardiac stimulator with a pin-type warning electrode.

Our invention may also be configured as a pin electrode, of a form more particularly described in U.S. patent application Ser. No. 08/532,961 and the continuation-in-part thereof, attorney docket number ITM-310-CIP, the disclosure of which is incorporated herein by reference. A pin electrode 90 utilizing our invention is illustrated affixed to the cardiac stimulator 10 in FIG. 5 and in exploded perspective view in FIG. 6. The pin electrode 90 comprises a cylindrical metal shaft 92 which is configured to make electrical contact with connections inside the socket 16. An insulating sheath 94 surrounds the shaft 92. The sheath 94 preferably has circumferential ridges 96 which help exclude body fluids from the socket 16. A warning electrode 98 connects to the shaft. In use, the shaft 92 and sheath 94 are inserted into the socket 16 of the stimulator 10 such that the warning electrode 98 lies against the header 14. This prevents the pin electrode 90 from rotating in the socket 16 and helps to avoid inadvertent disassembly of the pin electrode 90 from the socket 16.

The warning electrode 98 comprises a front face 100 which lies generally perpendicular to an axis of the shaft 92. The shaft 92 may protrude into the face 100 and be welded thereon. In our preferred embodiment, the face 100 has a curved upper edge 102 and a generally straight lower edge 104. From the upper edge 102, a lip 106 extends backwardly, partially surrounding the shaft 92. The face 100 and lip 106 form a hood shape which fits around a portion of the header 14, shown in FIG. 5 as a part of the cardiac stimulator 10. Provision may be made in the hood to accommodate methods for attaching the pin in the header. For example, a sidelock attachment apparatus is described by Frey et al. in U.S. Pat. No. 4,860,750 to accommodate such an attachment mechanism, a notch 108 may be provided on one side of the lip 106.

Figure 7:
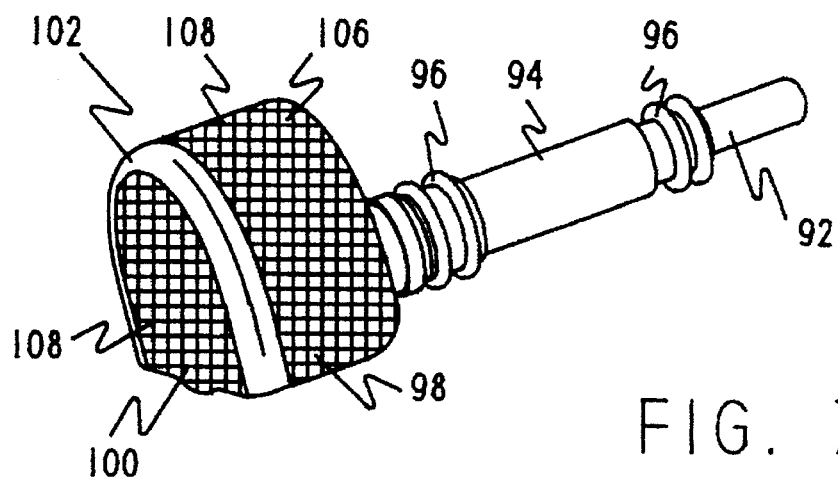
FIG. 7 is a perspective view of the pin electrode of FIG. 6 with conductive corners.

To provide a stimulating surface having a length and width as described above, only a portion of the head or stimulating electrode is exposed, and particularly only corners or edges are exposed. This is illustrated particularly in FIGS. 7 through 9. It is known in the pacemaker art to coat the cans of pacemakers with parylene, forming a nonconductive coating on the pacemaker, and then to etch or otherwise remove a portion of the parylene, exposing a small part of the pacemaker can which acts as an indifferent electrode. Similar processes can be used on the pin of our invention to coat the hood or electrode 98. As illustrated in FIG. 7, a parylene layer 108 would coat both the face 100 and lip 106 of the hood-like electrode. This would render most of the electrode nonconductive. Selected portions of the front face 96 and the lip 106 can then be exposed by, for example, etching to provide a relatively small, well defined electrode area which would be both likely to come in contact with adjacent tissue and would support a high electric current density to stimulate that tissue. In particular, the corner 102 can be so exposed.

Figure 8:
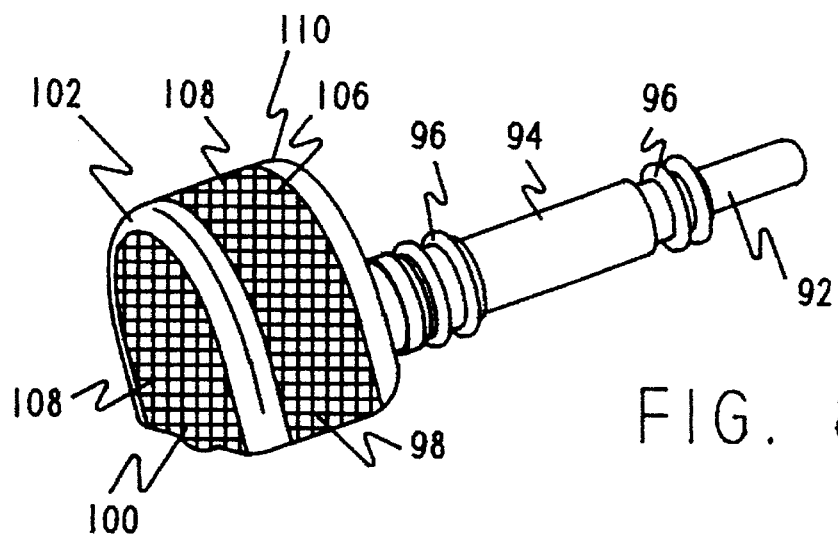
FIG. 8 is a perspective view of the electrode of FIG. 6 with conductive corner and edge.
Figure 9:
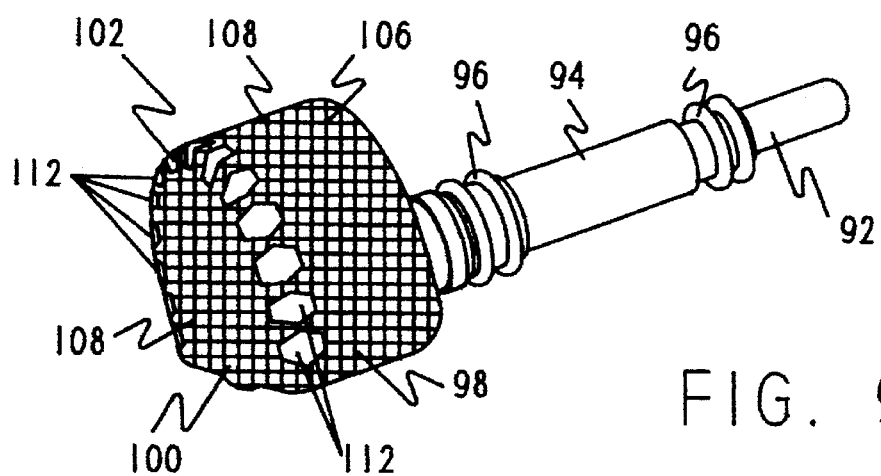
FIG. 9 is a perspective view of the pin electrode of FIG. 6 with partially exposed corners.

An alternative embodiment is illustrated in FIG. 8. In addition to an exposed edge or corner 102, a rear edge 110 of the lip 106 has also been exposed. A final embodiment is illustrated in FIG. 9 wherein only selected portions of the corner 102 have been exposed forming a series of point electrodes 112 along the corner. Such a configuration could also be employed on an edge of the hood electrode 98. The effect of the series of point electrodes 112 is to form a stimulating surface with an effective length longer than an effective width of the surface.

Our invention may be embodied in other specific forms without departing from the spirit or essential characteristics thereof. Present embodiment is therefore considered in all respects to be illustrative and not restrictive, the scope of our invention being indicated by the appended claims whether by the foregoing description and all changes which come within the meaning and range of equivalency of the claims are therefore intended to be embraced therein.

We claim as our invention:

1. An implantable cardiac therapy system comprising
   means for producing a cardiac therapy,
   a header on said therapy producing means,
   at least one socket in said header on said therapy producing means, said socket having electrical connections therein electrically connected to said therapy producing means,
   means for detecting a predetermined condition,
   means for producing a physiologic warning stimulation to warn said patient of said detected condition, and
   a warning electrode on said cardiac therapy system, said electrode being electrically connected to said means for producing a physiologic warning stimulation and having at least one stimulating surface having a width and a length orthogonal to said width, said length at least twice said width.

2. The implantable cardiac therapy system according to claim 1 wherein said length is at least four times said width.

3. The implantable cardiac therapy system according to claim 1 wherein said stimulating surface comprises an edge.

4. The implantable cardiac therapy system according to claim 1 wherein said stimulating surface is curved along said length.

5. The implantable cardiac therapy system according to claim 1 wherein said warning electrode comprises a first stimulating surface and a second stimulating surface.

6. The implantable cardiac therapy system according to claim 5 wherein the lengths of said first and second stimulating surfaces are substantially parallel to one another.

7. The implantable cardiac therapy system according to claim 1, wherein said cardiac therapy system comprises an hermetically sealed case having a front side, a back side and edge connecting said front side and said back side and wherein said warning electrode is disposed on at least one of said sides.

8. The implantable cardiac therapy system according to claim 7 wherein said warning electrode comprises a first stimulating surface and a second stimulating surface.

9. The implantable cardiac therapy system according to claim 8 wherein the lengths of said first and second stimulating surfaces are substantially parallel to one another.

10. The implantable cardiac therapy system according to claim 7 wherein said warning electrode extends on both said sides.

11. The implantable cardiac therapy system according to claim 10 wherein said warning electrode extends continuously from said front side to said back side.

12. The implantable cardiac therapy system according to claim 11 wherein said warning electrode comprises a first stimulating surface and a second stimulating surface, both said first and second stimulating surfaces extending continuously from said front side to said back side.

13. The implantable cardiac therapy system according to claim 12 wherein the lengths of said first and second stimulating surfaces are substantially parallel to one another.

14. The implantable cardiac therapy system according to claim 10 wherein said warning electrode is mounted on said header.

15. The implantable cardiac therapy system according to claim 14 wherein said warning electrode extends continuously from said front side to said back side.

16. The implantable cardiac therapy system according to claim 15 wherein said warning electrode comprises a first stimulating surface and a second stimulating surface, both said first and second stimulating surfaces extending continuously from said front side to said back side.

17. The implantable cardiac therapy system according to claim 16 wherein the lengths of said first and second stimulating surfaces are substantially parallel to one another.

18. The implantable cardiac therapy system according to claim 1, further comprising at least two sockets in said header, each socket having electrical connections therein electrically connected to said therapy producing means and a pin electrode, said pin electrode having a shaft configured to be inserted into at least one of said sockets and to make electrical contact with said electrical connections therein, said pin electrode having a head carrying said warning electrode substantially immediately adjacent said socket when said shaft is inserted in said socket.

19. The implantable cardiac therapy system according to claim 18 wherein said length is at least four times said width.

20. The implantable cardiac therapy system according to claim 18 wherein said stimulating surface comprises an edge.

21. The implantable cardiac therapy system according to claim 18 wherein said head has a first non-conductive surface and a second non-conductive surface, said surfaces forming a corner therebetween and wherein at least selected areas of said corner are electrically conductive and wherein said stimulating surface comprises said selected areas of said corner.

22. The implantable cardiac therapy system according to claim 19 wherein substantially all of said corner is electrically conductive.

23. A pin electrode adapted for use with an implantable cardiac stimulation system, said cardiac stimulation system having a case containing electrical means for producing a stimulation therapy and a header on said case, said header containing at least one socket having electrical connections therein electrically connected to said means for producing a stimulation therapy, said pin electrode having a shaft configured to be inserted into said socket and to make electrical contact with the electrical connections therein and having electrode means substantially immediately adjacent said socket when said shaft is inserted in said socket, wherein said electrode means comprises an electrically conductive warning electrode, said warning electrode having a stimulating surface with a width and a length orthogonal to said width, said length being at least twice said width.

24. The implantable cardiac therapy system according to claim 23 wherein said length is at least four times said width.

25. The implantable cardiac therapy system according to claim 23 wherein said stimulating surface comprises an edge.

26. The implantable cardiac therapy system according to claim 23 wherein said head has a first non-conductive surface and a second non-conductive surface, said surfaces forming a corner therebetween and wherein at least selected areas of said corner are electrically conductive and wherein said stimulating surface comprises said selected areas of said corner.

27. The implantable cardiac therapy system according to claim 26 wherein substantially all of said corner is electrically conductive.

* * * * *